US011344258B2

(12) United States Patent
Bushnell et al.

(10) Patent No.: US 11,344,258 B2
(45) Date of Patent: *May 31, 2022

(54) SENSING CONTACT FORCE RELATED TO USER WEARING AN ELECTRONIC DEVICE

(71) Applicant: Apple Inc., Cupertino, CA (US)

(72) Inventors: Tyler S. Bushnell, Mountain View, CA (US); Steven J. Martisauskas, San Francisco, CA (US); Erik G. de Jong, San Francisco, CA (US); Andrzej T. Baranski, Santa Clara, CA (US); Serhan O. Isikman, Sunnyvale, CA (US); Steven J. Banaska, San Francisco, CA (US); Todd K. Whitehurst, Cupertino, CA (US); Ming L. Sartee, Morro Bay, CA (US)

(73) Assignee: Apple Inc., Cupertino, CA (US)

( * ) Notice: Subject to any disclaimer, the term of this patent is extended or adjusted under 35 U.S.C. 154(b) by 642 days.

This patent is subject to a terminal disclaimer.

(21) Appl. No.: 16/369,873

(22) Filed: Mar. 29, 2019

(65) Prior Publication Data

US 2019/0223802 A1 Jul. 25, 2019

Related U.S. Application Data

(63) Continuation of application No. 14/867,311, filed on Sep. 28, 2015, now Pat. No. 10,285,645.

(51) Int. Cl.
*A61B 5/00* (2006.01)
*G01L 1/14* (2006.01)
*A61B 5/021* (2006.01)

(52) U.S. Cl.
CPC ............ *A61B 5/6843* (2013.01); *A61B 5/681* (2013.01); *G01L 1/142* (2013.01); *A61B 5/021* (2013.01);

(Continued)

(58) Field of Classification Search
CPC ....... A61B 5/6843; A61B 5/681; A61B 5/021; A61B 5/412; A61B 5/4872; A61B 2562/0261; G01L 1/142

(Continued)

(56) References Cited

U.S. PATENT DOCUMENTS 7,784,366 B2 8/2010 Daverman et al.
8,033,916 B2 10/2011 Caldwell et al.
(Continued)

FOREIGN PATENT DOCUMENTS

CN 103393411 11/2013

OTHER PUBLICATIONS

Dementyev et al., "WristFlex Low-Power Gesture Input with Wrist-Worn Pressure Sensors," UIST 2014, Oct. 5-8, 2014, Honolulu, Hawaii, 6 pages.

*Primary Examiner* — May A Abouelela
(74) *Attorney, Agent, or Firm* — Brownstein Hyatt Farber Schreck, LLP

(57) ABSTRACT

A wearable electronic device includes a body, a housing component, a band operable to attach the body to a body part of a user, and a force sensor coupled to the housing component. The force sensor is operable to produce a force signal based on a force exerted between the body part of the user and the housing component. A processing unit of the wearable electronic device receives the force signal from the force sensor and determines the force exerted on the housing component based thereon. The processing unit may use that force to determine a tightness of the band, determine health information for the user, adjust determined force exerted on a cover glass, and/or to perform various other actions.

20 Claims, 7 Drawing Sheets

(52) U.S. Cl.
CPC ............. *A61B 5/412* (2013.01); *A61B 5/4872* (2013.01); *A61B 2562/0261* (2013.01)

(58) Field of Classification Search
USPC ........................................................ 600/587
See application file for complete search history.

(56) References Cited

U.S. PATENT DOCUMENTS

| | | |
|---|---|---|
| 8,541,745 B2 | 9/2013 | Dickinson et al. |
| 8,684,900 B2 | 4/2014 | Tran |
| 8,764,651 B2 | 7/2014 | Tran |
| 8,776,418 B1 | 7/2014 | Martinez et al. |
| 8,781,791 B2 | 7/2014 | Panther |
| 8,919,019 B2 | 12/2014 | Martinez et al. |
| 8,920,332 B2 | 12/2014 | Hong et al. |
| 9,144,273 B2 | 9/2015 | Wu et al. |
| 9,198,617 B2 | 12/2015 | Kurzweil et al. |
| 9,274,507 B2 | 3/2016 | Kim et al. |
| 9,282,903 B2 | 3/2016 | Iijima et al. |
| 9,311,792 B2 | 4/2016 | Kosonen et al. |
| 9,572,533 B2 | 2/2017 | Venkatraman et al. |
| 9,609,921 B1 * | 4/2017 | Feinstein ............. A44C 5/2071 |
| 9,781,984 B2 | 10/2017 | Baranski et al. |
| 9,875,008 B2 * | 1/2018 | Cauwels ............. G06F 3/04845 |
| 9,877,685 B2 | 1/2018 | Kwon et al. |
| 9,898,120 B2 * | 2/2018 | Rhee ..................... G06F 3/0488 |
| 9,968,294 B2 | 5/2018 | Bichel et al. |
| 10,061,350 B2 * | 8/2018 | Magi ..................... A44C 5/0069 |
| 10,206,623 B2 | 2/2019 | Harrison-Noonan et al. |
| 2005/0075542 A1 | 4/2005 | Goldreich |
| 2006/0100530 A1 | 5/2006 | Kliot et al. |
| 2008/0171915 A1 * | 7/2008 | Kawajiri ............. A61B 5/7221 600/300 |
| 2010/0024573 A1 * | 2/2010 | Daverman ............. G01L 1/142 73/862.626 |
| 2011/0125037 A1 * | 5/2011 | Iijima .................... A61B 5/681 600/500 |
| 2013/0053661 A1 | 2/2013 | Alberth et al. |
| 2014/0031705 A1 * | 1/2014 | Kurzweil ................. A61B 5/01 600/506 |
| 2014/0180137 A1 | 5/2014 | Stivoric et al. |
| 2014/0174958 A1 * | 6/2014 | Martinez ................ G06F 15/00 206/37 |
| 2014/0200412 A1 * | 7/2014 | Martinez ................. A61B 5/742 600/300 |
| 2014/0257050 A1 * | 9/2014 | Kuroda .................. A61B 5/1116 600/301 |
| 2014/0296749 A1 * | 10/2014 | Reid, Jr. ................... D04B 1/12 600/587 |
| 2014/0298679 A1 | 10/2014 | Reid, Jr. et al. |
| 2015/0135410 A1 * | 5/2015 | Wu ...................... A44C 5/0061 2/338 |
| 2015/0173633 A1 * | 6/2015 | Shimizu ............. A61B 5/02427 600/479 |
| 2015/0187188 A1 * | 7/2015 | Raskin .............. H04M 1/72412 340/407.1 |
| 2015/0297132 A1 * | 10/2015 | Bichel .................. A61B 5/4836 600/301 |
| 2015/0305675 A1 | 10/2015 | Miller et al. |
| 2015/0342525 A1 * | 12/2015 | Justice ................. A61B 5/0024 600/479 |
| 2016/0058388 A1 * | 3/2016 | Kwon .................. A61B 5/0533 600/547 |
| 2016/0066844 A1 * | 3/2016 | Venkatraman ....... A61B 5/0002 702/141 |
| 2016/0071408 A1 * | 3/2016 | Jiao ...................... A61B 5/1118 600/300 |
| 2016/0074649 A1 * | 3/2016 | Williams ............. A61B 5/6803 600/587 |
| 2016/0143584 A1 * | 5/2016 | Inagaki .............. A61B 5/02416 600/300 |
| 2016/0256116 A1 * | 9/2016 | Baik .................... A61B 5/0059 |
| 2017/0086743 A1 | 3/2017 | Bushnell et al. |
| 2018/0014785 A1 * | 1/2018 | Li ........................ A61B 5/6844 |
| 2018/0232063 A1 * | 8/2018 | Park ...................... G06F 3/0412 |

* cited by examiner

SENSING CONTACT FORCE RELATED TO USER WEARING AN ELECTRONIC DEVICE

CROSS-REFERENCE TO RELATED APPLICATION

This application is a continuation of U.S. patent application Ser. No. 14/867,311, filed Sep. 28, 2015, entitled "Sensing Contact Force Related to User Wearing an Electronic Device," the contents of which are incorporated herein by reference as if fully disclosed herein.

FIELD

The described embodiments relate generally to wearable electronic devices. More particularly, the present embodiments relate to sensing the force applied to a wearable electronic device by a user's body part when a user is wearing the wearable electronic device.

BACKGROUND

Users frequently encounter a variety of different electronic devices in the modern world. Such electronic devices include computers, media players, entertainment systems, displays, communication systems, and so on. Many electronic devices, such as laptop computers, tablet computers, and smart phones, may be portable.

Some electronic devices, referred to as "wearable electronic devices," may be configured to be worn by a user. In some cases, such a wearable electronic device may include one or more bands, straps, or other attachment mechanisms that may be used to attach the wearable electronic device to a user's body part. For example, a wrist worn wearable electronic device may include a band that can be used to secure the wearable electronic device to a user's wrist.

Wearable electronic devices may include a variety of components. For example, wearable electronic devices may include input devices that a user can manipulate by touch. By way of another example, wearable electronic devices may include various sensors, such as sensors that may be used to detect information about the user.

SUMMARY

The present disclosure relates to wearable electronic devices that sense the force applied to the wearable electronic device by a user's body part when the user is wearing the wearable electronic device. The wearable electronic device may include a body, a housing component, and a band or other attachment mechanism operable to attach the body to the body part of a user. A force sensor may be positioned between the housing component and the body that produces force signals based on a force exerted between the user's body part and the housing component. A processing unit may receive the force signals and process them to perform various actions.

In various embodiments, a wearable electronic device includes a body, a housing component coupled to the body, a band operable to attach the body to a body part of a user, a force sensor coupled to the housing component that is operable to produce a force signal based on a force exerted between the body part of the user and the housing component, and a processing unit communicably coupled to the force sensor. The processing unit may be operable to determine a tightness of the band based on the force signal received from the force sensor.

In some examples, the force sensor may be a strain gauge mounted to a deflection element that is connected to the body and the housing component. In such an example, the force signal may indicate deflection of the deflection element based on strain data detected by the strain gauge.

In various examples, the force sensor may be a gasket positioned between the body of the wearable electronic device and the housing component. The gasket may include a pair of electrodes separated by a deformable material. In such an example, the force signal may indicate a capacitance between the pair of electrodes. The pair of electrodes may form a capacitor and the force signal may represent a capacitance of the capacitor.

In one or more examples, the force sensor may include an electrode. In such an example, the force signal may indicate a capacitance between the electrode and the body part of the user. The electrode and the body part of the user may form a capacitor and the force signal may represent a capacitance of the capacitor. The electrode may be coupled to one of the housing component, the body, or a circuit board coupled to the body. In some embodiments, the electrode may be formed of indium tin oxide, nanostructures, nanomesh, nanowires, a conductive film, and so on.

In some examples, the wearable electronic device may further include a circuit board coupled to the body, and the force sensor may include a first electrode coupled to the housing component and a second electrode coupled to the circuit board. In such an example, the force signal received from the first and second electrodes may indicate a capacitance between the first electrode and the second electrode. In various cases of such an example, the first electrode may be a first set of electrodes and the second electrode may be a second set of electrodes. In some cases of this example the housing component may be flexible.

In some embodiments, a wearable electronic device may include a body, a surface component coupled to the body, a health sensor coupled to the body, a force sensor coupled to the surface component, and a processing unit communicably coupled to the force sensor. The surface component may be positioned adjacent to a body part of a user when the wearable electronic device is worn. The health sensor may be operable to obtain a measurement of the body part of the user. The force sensor may be operable to produce a force signal based on a force exerted between the body part of the user and the surface component. The processing unit may be operable to determine health information for the user based on the force signal received from the force sensor and the measurement obtained by the health sensor.

In one or more examples, the health information may include at least one of a swelling indication, a blood pressure, a body fat indication, an allergic reaction indication, a hydration indication, or an edema indication.

In various examples, the processing unit may determine whether the measurement obtained by the health sensor is accurate based on the force signal.

In some examples, the wearable electronic device may include a band operable to attach the body to the body part of the user. In such examples, the processing unit may determine a tightness of the band based on the force signal. If the tightness of the band is within a range of force values, the processing unit may determine the measurement obtained by the health sensor is accurate. If the tightness of the band is outside the range of force values, the processing unit may determine the measurement obtained by the health sensor is inaccurate.

In various examples, the wearable electronic device may further include a band operable to attach the body to the body part of the user and a band tightness adjustment mechanism. In such an example, the processing unit may determine a tightness of the band based on the force signal received from the force sensor and cause the tightness of the band to be altered using the band tightness adjustment mechanism. In various cases, the processing unit may provide a notification to the user by causing the tightness of the band to be altered.

In one or more embodiments, a wearable electronic device may include a body, a cover glass coupled to the body, a plate coupled to the body, a first force sensor coupled to the cover glass, a second force sensor coupled to the plate, and a processing unit communicably coupled to the first and second force sensors. The plate may be positioned adjacent to a body part of a user when the wearable electronic device is worn. The first force sensor may be operable to produce a first force signal based on a first force exerted on the cover glass. The second force sensor may be operable to produce a second force signal based on a second force exerted between the body part of the user and the plate. The processing unit may be operable to determine an amount of the first force based on the first force signal, determine an amount of the second force based on the second force signal, and adjust the amount of the first force based on the second force signal.

In various examples, the processing unit may be further operable to adjust the amount of the second force based on the first force signal. For example, the first force exerted on the cover glass may cause additional force to be exerted between the body part of the user and the plate. In order to determine the second force exerted between the body part of the user and the plate without the additional force being exerted due to the first force exerted on the cover glass, the amount of the second force may be adjusted based on the first force signal to remove the influence of the first force.

In some examples, the processing unit may be further operable to determine a pressure to which the body is exposed based on the first force signal received from the first force sensor and the second force signal received from the second force sensor, such as a water pressure.

In one or more examples, the processing unit may determine whether the wearable electronic device is worn by the user based on the second force signal received from the second force sensor.

BRIEF DESCRIPTION OF THE DRAWINGS

The disclosure will be readily understood by the following detailed description in conjunction with the accompanying drawings, wherein like reference numerals designate like structural elements, and in which.

DETAILED DESCRIPTION

Reference will now be made in detail to representative embodiments illustrated in the accompanying drawings. It should be understood that the following descriptions are not intended to limit the embodiments to one preferred embodiment. To the contrary, it is intended to cover alternatives, modifications, and equivalents as can be included within the spirit and scope of the described embodiments as defined by the appended claims.

The description that follows includes sample systems, methods, and apparatuses that embody various elements of the present disclosure. However, it should be understood that the described disclosure may be practiced in a variety of forms in addition to those described herein.

The following disclosure relates to wearable electronic devices operable to sense the force applied to the wearable electronic device by body part of a user when the user is wearing the wearable electronic device. The wearable electronic device may include a body, a housing component (such as a plate, a curved plate, or other surface component), and a band or other attachment mechanism operable to attach the body to the body part of a user. A force sensor may be positioned between the housing component and the body such that it produces force signals based on a force exerted between the user's body part and the housing component. A processing unit may receive the force signals and process them to perform various actions.

For example, the processing unit may process the force signals to determine a tightness of the band, such as for automatic band adjustment. By way of another example, the processing unit may use the force signals to determine health information for the user, such as in combination with measurements of the body part obtained via a health sensor included in the body. By way of still another example, the body may include an input mechanism (such as a touch surface including a cover glass) that interprets the force of a user's touch as input and the processing unit may use the force signals and signals from the input mechanism to adjust determinations of force applied to the housing component or input mechanism. Various uses for the force signals from the force sensor are possible and contemplated.

These and other embodiments are discussed below with reference to FIGS. 1A-11. However, those skilled in the art will readily appreciate that the detailed description given herein with respect to these Figures is for explanatory purposes only and should not be construed as limiting.

Figure 1A:
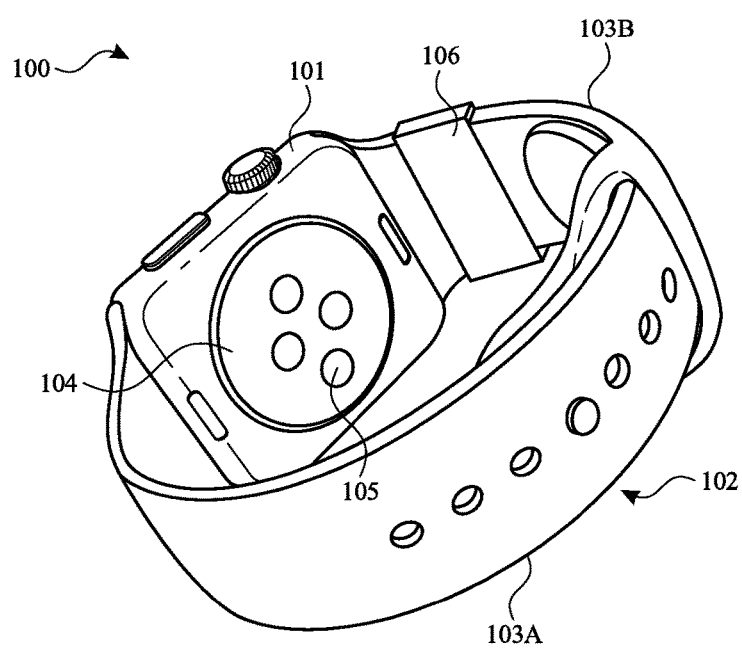
FIG. 1A shows a wearable electronic device that may sense the force exerted by a body part of a user on the wearable electronic device when the user is wearing the wearable electronic device.

FIG. 1A shows a wearable electronic device 100 that may sense the force applied to the wearable electronic device 100 when the user is wearing the wearable electronic device 100.

Figure 1B:
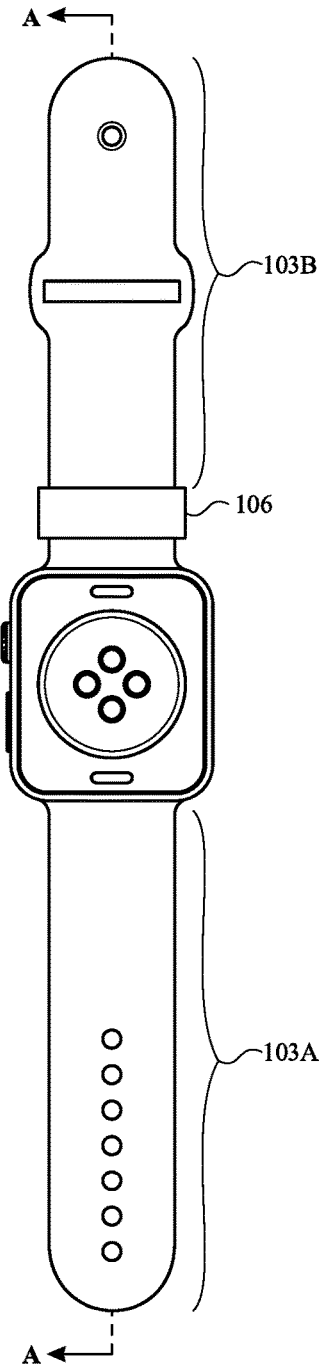
FIG. 1B shows the wearable electronic device of FIG. 1A from the back with the band opened.

FIG. 1B shows the wearable electronic device 100 of FIG. 1A from the back with the band 102 opened.

With reference to FIGS. 1A and 1B, the wearable electronic device 100 may include a main body 101 that is operable to be coupled to the body part of a user (such as a wrist) via the band 102 or other attachment mechanism. For example, the band 102 may be operable to attach to the main body 101 and to the body part of the user, thus attaching the main body 101 to the body part of the user. A housing component 104 (such as a plate, a curved plate, or other surface component) may be coupled to the main body 101 in such a way that the wearable electronic device 100 may determine the amount of force exerted by the user's body part contacting the housing component 104 when the band 102 is attached to user. The wearable electronic device 100 may utilize the determined force in a variety of ways that will be discussed in detail below.

The housing component 104 may be a sensor plate associate with a sensor of the main body 101. As such, the housing component 104 may include one or more sensor windows 105 associated with the operation of that sensor.

The band 102 may include a first band portion 103A and a second band portion 103B. The second band portion 103B may include a band tightening mechanism 106 that is operable to tighten the band 102 around the user's body part. However, it is understood that this is an example. In various implementations, the first band portion 103A may include such a tightening mechanism instead of and/or in addition to the second band portion 103B. Further, in some implementations, the band 102 may not have separate portions and/or may have more than two portions without departing from the scope of the present disclosure.

Figure 2A:
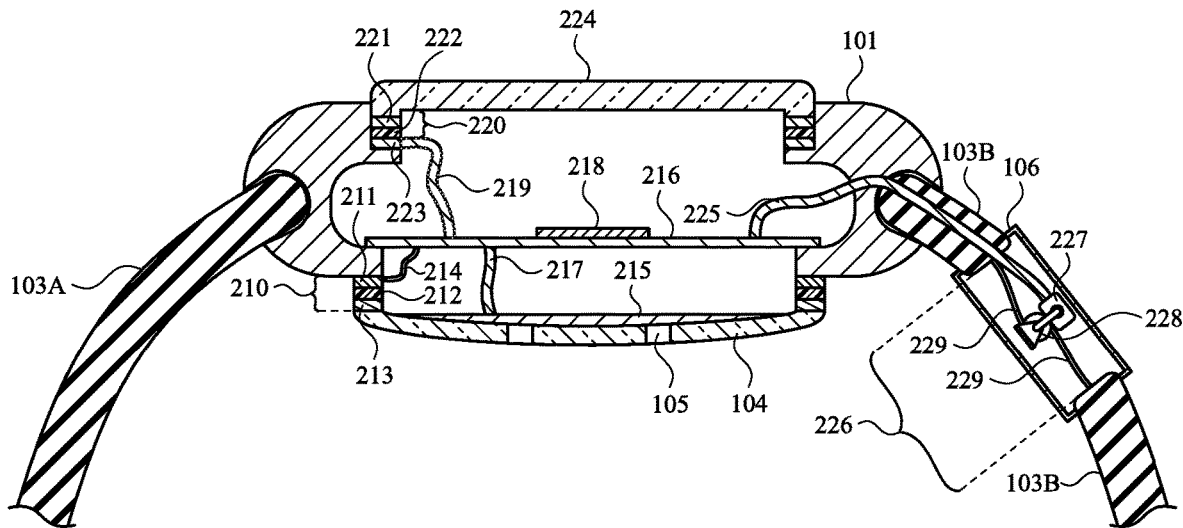
FIG. 2A shows an example cross-sectional view of the wearable electronic device of FIG. 1B, taken along line A-A of FIG. 1B.

FIG. 2A shows an example cross-sectional view of the wearable electronic device 100 of FIG. 1B, taken along line A-A of FIG. 1B. The housing component 104 may be coupled to the main body 101 via a housing component force sensor 210 (such as via one or more adhesives, springs, and/or other attachment mechanisms). The housing component force sensor 210 may include one or more first electrodes 211 separated from one or more second electrodes 213 by a deformable material 212 (such as silicone, an air gap, and so on). For example, the first and second electrodes 211 and 213 may be discrete electrodes or sets of electrodes. The first and second electrodes 211 and 213 may be included in a flexible circuit layer. The first and second electrodes 211 and 213 may be aligned to form a capacitor. Force exerted on the housing component 104 may deform the deformable material 212, changing the proximity of the first and second electrodes 211 and 213 and thus a capacitance of a capacitor formed by the first and second electrodes 211 and 213 (e.g., the capacitance between the first and second electrodes 211 and 213). The housing component force sensor 210 may generate force signals that represent the changes in capacitance.

A processing unit 218 may be disposed within the main body 101. In this example, the processing unit 218 may be disposed on a printed circuit board 216 mounted within the body such as via one or more adhesives and/or other attachment mechanisms. The printed circuit board 216, and thus the processing unit 218, may be connected to the housing component force sensor 210 via a flex circuit 214 (and/or other electrical or communication connection). The processing unit 218 may receive the force signal generated by the housing component force sensor 210 via the flex circuit 214 and the printed circuit board 216. The processing unit 218 may associate various exerted force values with various capacitance changes. As such, the processing unit 218 may analyze the force signal to determine the force exerted on the housing component 104.

The force determined by the processing unit 218 by analyzing force signals may be a non-binary value. The processing unit 218 may analyze the force signals to determine forces across a range of force values as opposed to detecting that a threshold amount of force is exerted. The processing unit 218 may analyze force signals to correlate data in the force signals to an amount of force applied out of a range of possible forces.

The processing unit 218 may utilize the determined force exerted on the housing component 104 for a variety of purposes. Examples that will be discussed in further detail below include determining a tightness of the band 102 (such as for automatic band adjustment, signaling a user to adjust, and so on), determining whether or not the wearable electronic device 100 is being worn, and obtaining user input (such as wrist movement gestures and so on), determining health information (using the determined force alone and/or in combination with measurements from a health sensor and/or other data). Additionally or alternatively, the processing unit 218 may utilize the determined force exerted on the housing component 104 in combination with force determined based on signals from another force sensor (such as to adjust one or both of the determined forces, to determine pressure based on both determined forces, and so on). However, it is understood that these are examples and that the processing unit 218 may utilize the determined force exerted on the housing component 104 for a variety of other purposes (such as in combination with data from one or more accelerometers, gyroscopes, altimeters, and so on) without departing from the scope of the present disclosure.

In some embodiments, the housing component force sensor 210 may function as a gasket, positioned in a perimeter between the main body 101 and the housing component 104, and forming a seal between the main body 101 and the housing component 104. Further, although the housing component force sensor 210 is described as a single force sensor, it is understood that this is an example. In various implementations, multiple housing component force sensors 210 may be positioned in a perimeter between the main body 101 and the housing component 104. The multiple housing component force sensors 210 may be part of a gasket or other structure that includes the housing component force sensors 210 with the deformable material 212 and/or other materials filling gaps in between the housing component force sensors 210. In such an implementation, the processing unit 218 may analyze and compare force signals from each housing component force sensor 210 to determine one or more forces exerted on the housing component 104 in various directions, at various positions, and so on.

Figure 2B:
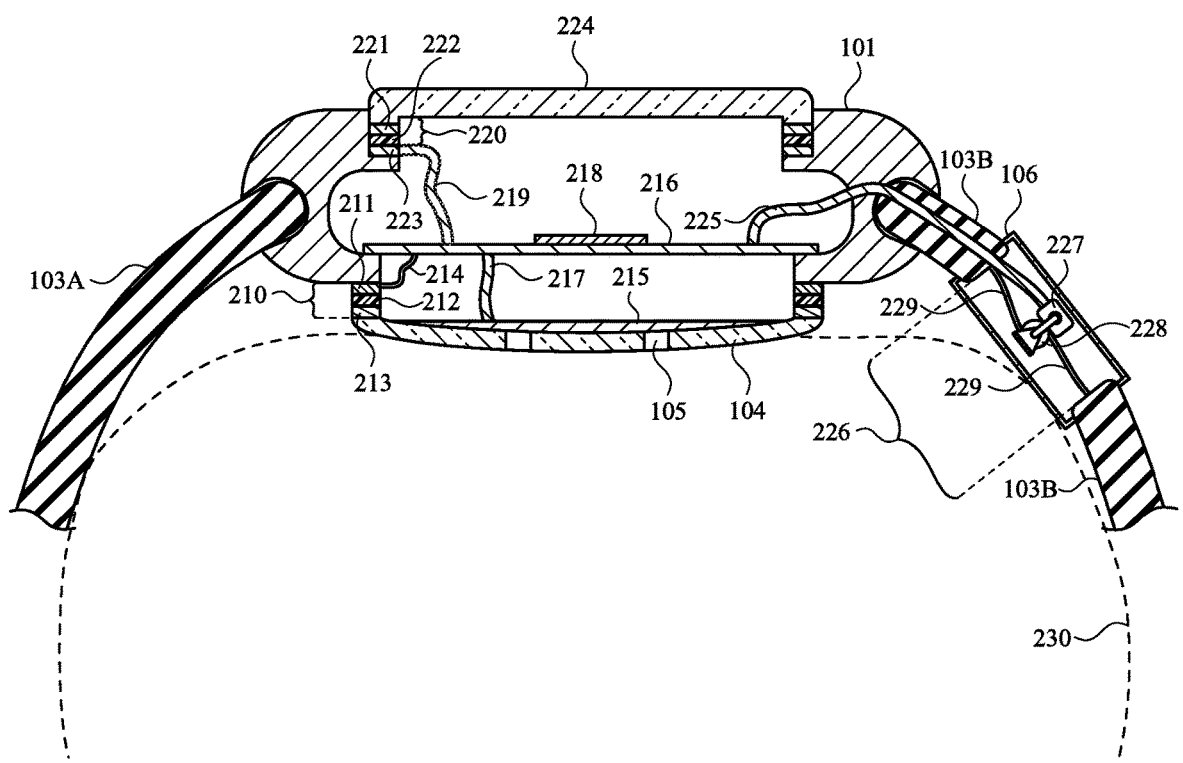
FIG. 2B shows the wearable electronic device of FIG. 2A on a user's body part.

As discussed above, the tightness of the band 102 may be determined by the processing unit 218 using the determined force exerted on the housing component 104. FIG. 2B shows the wearable electronic device 100 of FIG. 2A on a user's body part 230 (depicted as the user's wrist, though this is merely an example and any body part may be used in other implementations). The user's body part 230 may exert force on the housing component 104. The force exerted by the user's body part 230 on the housing component 104 may be proportional to the tightness of the band 102. In other words, the tighter the band 102, the more force exerted by the user's body part 230 on the housing component 104. Similarly, the looser the band 102, the less force exerted by the user's body part 230 on the housing component 104.

The tightness of the band 102 may be significant for user comfort, ensuring the wearable electronic device 100 stays attached, and so on. As such, the tightness of the band 102 may be monitored for user comfort based on default tightness settings, user specified comfort settings, and so on. If the band 102 is too tight or too loose, the processing unit 218 may provide output instructing the user to adjust the band 102, automatically adjust the band 102 using a mechanism such as the band tightening mechanism 106 discussed below, and/or perform other such actions.

The tightness of the band 102 may be significant for reasons other than comfort. In various implementations, the wearable electronic device 100 may include one or more sensors and/or other components whose operation may depend on tightness of the band 102. In such implementations, the processing unit 218 may provide adjustment instructions and/or adjust the band 102 to improve operation of such sensors and/or other components.

For example, a health sensor 215 may be coupled to the housing component 104. In one embodiment, the health sensor 215 may be a photoplethysmogram (PPG) sensor that emits light through the sensor windows 105 into the user's body part 230 and receives the portion of the transmitted light that is reflected back from the user's body part 230. The health sensor 215 may be coupled to the processing unit 218 via the printed circuit board 216 and a flex circuit 217 (and/or other electrical or communication connection) and may transmit measurements regarding the received light to the processing unit 218. The operation of the health sensor 215 may be affected by the tightness of the band 102. For example, the health sensor 215 may transmit less accurate measurements if the band 102 is too loose. As such, the processing unit 218 may provide adjustment instructions and/or tighten the band 102 to improve operation of the health sensor 215.

Figure 2C:
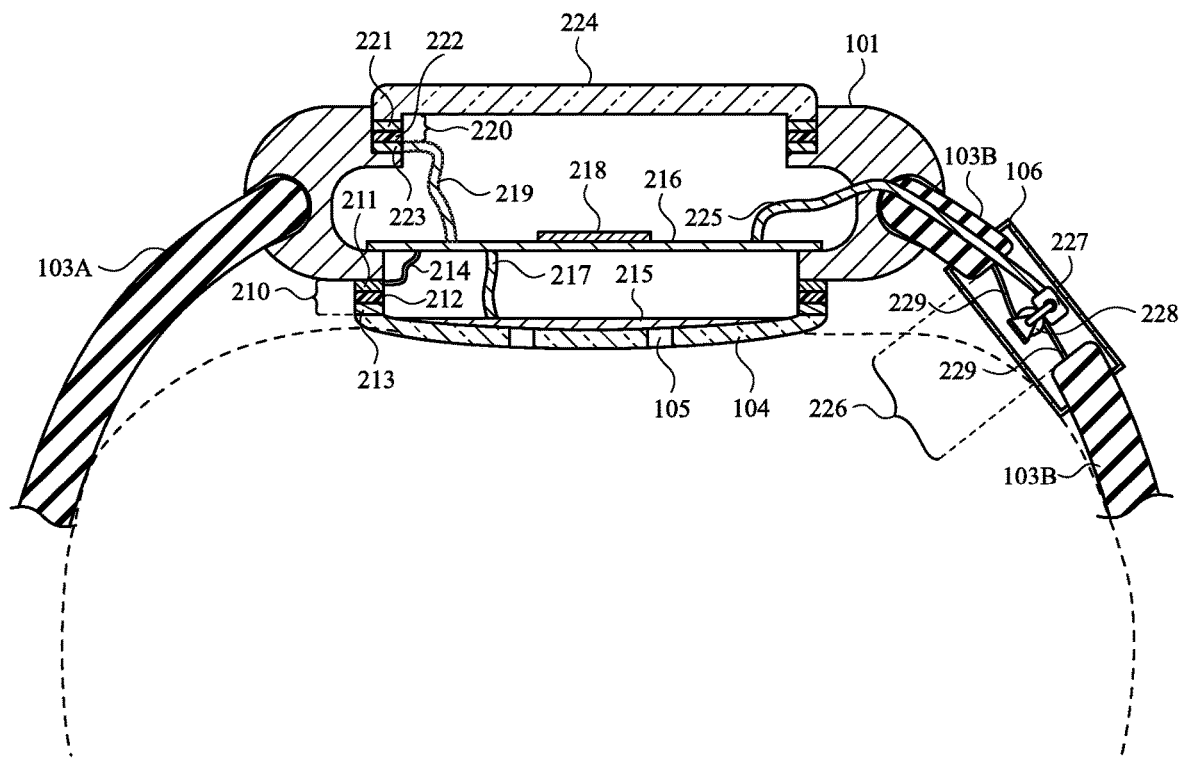
FIG. 2C shows the wearable electronic device of FIG. 2B after tightening of the band.

FIG. 2C shows the wearable electronic device 100 of FIG. 2B after tightening of the band 102 by the band tightening mechanism 106 as controlled by the processing unit 218. In this example, the second band portion 103B may be divided into sections separated by a gap 226. The sections may be connected to a winch mechanism 228 by cords 229 (and/or wires or other joining mechanisms). The winch mechanism 228 may be controlled by a motor 227, which may be connected to the printed circuit board 216, and thus the processing unit 218, via a flex circuit 225 (and/or other electrical or communication connection). Thus, the processing unit 218 may control the winch mechanism 228 to roll and/or unroll the cords 229 to bring the sections closer and narrow the gap 226 (see FIG. 2C) and/or to allow the sections to move further apart and expand the gap 226 (See FIG. 2B).

However, it is understood that the band tightening mechanism 106 is an example. Other band tightening mechanisms 106 constructed from various different components functioning under various different principles of operation can be used without departing from the scope of the present disclosure. For example, in some implementations, a memory wire such as Nitinol may be embedded in the band 102. The processing unit 218 may cause current to be provided to such a memory wire in order to change the shape of the memory wire, thus adjusting the tightness of the band 102.

Moreover, as discussed above, the processing unit 218 may utilize the determined force exerted on the housing component 104 to determine whether or not the wearable electronic device 100 is currently being worn. In various implementations, the processing unit 218 may operate in different states depending on whether or not the wearable electronic device 100 is currently worn (such as an active state if worn and a sleep or lower power state if unworn). In such implementations, the processing unit 218 may determine that the wearable electronic device 100 is worn if the determined force exerted on the housing component 104 is above a threshold force value and that the wearable electronic device 100 is unworn if the determined force exerted on the housing component 104 is below the threshold force value.

As also discussed above, the processing unit 218 may utilize the determined force exerted on the housing component 104 to obtain user input. For example, different movements of the user's body part 230 (such as bending of the wrist, flexing of the wrist, and so on) may exert different forces on the housing component 104. The processing unit 218 may analyze the determined force in order to determine how the user's body part 230 has moved. These different movements may be interpreted as gestures that are associated with different inputs. As such, the user may provide particular input to the processing unit 218 by making particular movements. For example, bending of the user's body part 230 may indicate to the processing unit 218 that the user wants to wake the wearable electronic device 100 from a sleep and/or otherwise low power state.

As further discussed above, the processing unit 218 may utilize the determined force exerted on the housing component 104 to determining health information. In some examples, the processing unit 218 may utilize the determined force by itself to determine health information. In other examples, the processing unit 218 may utilize the determined force in combination with measurements from a health sensor 215 and/or data from other sensors or devices (such as a camera, an accelerometer, and so on).

In some implementations, the processing unit 218 may determine a tightness of the band 102 based on the determined force over time. This determined tightness over time may be used to determine size changes in the user's body part 230 over time. Using such data, the processing unit 218 may be able to determine and/or detect an indication of a user's body fat, an indication of blood pressure, an indication of a pulse rate, an indication of swelling (such as caused by an allergic reaction, perhaps to a material used in the wearable electronic device 100), an indication of an allergic reaction, an indication of hydration (such as by relaxation of swelling over time), an indication of conditions such as edema or cutaneous edema, and so on. In various implementations, the processing unit 218 may utilize the determined tightness in combination with measurements by the health sensor 215, such as a PPG sensor, to determine health information of the user such as blood perfusion.

In still other implementations, the processing unit 218 may receive measurements from the health sensor 215. However, as described earlier, the measurements transmitted by the health sensor 215 may be inaccurate or less accurate if the band 102 is too loose or too tight. As such, the processing unit 218 may disregard measurements from the health sensor 215 if the determined force exerted on the housing component 104 indicates the band 102 is too loose or too tight.

Alternatively, the processing unit 218 may attempt to obtain a replacement measurement from the health sensor 215 if the determined force exerted on the housing component 104 indicates the band 102 is too loose or too tight. In such an example, measurements may be discarded if obtained from the health sensor 215 when the determined force exerted on the housing component 104 indicates the band 102 is too loose or too tight. In various implementations, the processing unit 218 may attempt to correct possible inaccuracies in the measurement.

As additionally discussed above, the processing unit 218 may utilize the determined force exerted on the housing component 104 in combination with force signals from another force sensor and/or data from other components. In various examples, the processing unit 218 may adjust the force determined from the other force sensor, adjust the determined force exerted on the housing component 104 based on the force determined from the other force sensor, determine pressure based on both determined forces, and so on.

For example, the wearable electronic device 100 may include an input device that interprets exerted force as input. As shown in FIGS. 2A-2C, the main body 101 may include a cover glass 224 (which may be part of a display such as a touch display) coupled to the main body 101. The cover glass 224 may be coupled to a cover glass force sensor 220 (such as via one or more adhesives or other attachment mechanisms). The cover glass force sensor 220 may include one or more first electrodes 221 separated from one or more second electrodes 223 by a deformable material 222 (such as silicone, an air gap, and so on). The first and electrodes 221 and 223 may form a capacitor. Force exerted on the cover glass 224 may deform the deformable material 222, changing a capacitance of the capacitor. The cover glass force sensor 220 may generate force signals indicating such changes in capacitance.

The cover glass force sensor 220 may be coupled to the printed circuit board 216, and thus the processing unit 218, via a flex circuit 219 (and/or other electrical or communication connection). The processing unit 218 may receive the force signals generated by the cover glass force sensor 220 via the flex circuit 219 and the printed circuit board 216. The processing unit 218 may associate various exerted force values with various capacitance changes. As such, the processing unit 218 may analyze the force signal to determine the amount of force exerted on the cover glass 224.

The processing unit 218 may evaluate both the first force signals generated by the housing component force sensor 210 corresponding to the force exerted on the housing component 104 and the second force signals generated by the cover glass force sensor 220 corresponding to the force exerted on the cover glass 224. In some implementations, the processing unit 218 may utilize one of the force signals to adjust the other of the force signals.

For example, a force exerted by a user on the cover glass 224 while the wearable electronic device 100 is worn may be different from a force applied while the wearable electronic device 100 is unworn. This may be because the wearable electronic device 100 is being pressed between the exertion of force on the cover glass 224 and the force between the user's body part 230 and the wearable electronic device 100 when the wearable electronic device 100 is worn. Conversely, force exerted on the cover glass 224 is not opposed by force between the user's body part 230 and the wearable electronic device 100 when the wearable electronic device 100 is unworn. Thus, the same amount of force exerted on the cover glass 224 could be determined to be different depending on whether or not the wearable electronic device 100 is worn at the time.

Therefore the processing unit 218 may modify the force detected on the cover glass 224 by any force detected on the housing component 104 in order for the processing unit 218 to determine force exerted on the cover glass 224 more uniformly regardless whether the wearable electronic device 100 is worn or not. For example, the force detected on the housing component 104 may be subtracted from the force detected on the cover glass 224. By way of another example, a modifier may be added to the force detected on the cover glass 224 when force is not detected on the housing component 104. Such a modifier may correspond to the force normally detected on the housing component 104 when the wearable electronic device 100 is worn.

By way of another example, if only the force exerted on the housing component 104 is used to determine the tightness of the band 102 while a user is exerting a force on the cover glass 224, the processing unit 218 may determine that the band 102 is tighter than it really is. This is because the force exerted on the cover glass 224 also exerts force on the housing component force sensor 210. To determine a more accurate tightness of the band 102, the processing unit 218 may subtract the force exerted on the cover glass 224 from the force exerted on the housing component 104 (and/or otherwise modify the determined force exerted on the housing component 104 based on the force exerted on the cover glass 224).

In other implementations, the processing unit 218 may use both forces in combination. For example, if force is exerted on both the housing component 104 and the cover glass 224 in relatively equal amounts, the processing unit 218 may determine that the forces are due to pressure as opposed to a user exerting force. The processing unit 218 may then evaluate the forces to determine a pressure to which the wearable electronic device 100 is subjected.

In some examples, the pressure may be hydrostatic pressure or water pressure, such as where the wearable electronic device 100 is submerged in water and/or other liquid. In such an example, the processing unit 218 may associate the forces detected with particular hydrostatic pressures in order to determine a depth of liquid in which the wearable electronic device 100 is immersed.

Although a particular configuration of the housing component 104, the main body 101, and the housing component force sensor 210 are shown and described, it is understood that this is an example. In other implementations, various configurations of the same, similar, and/or different components may be utilized without departing from the scope of the present disclosure. For example, FIGS. 3-7 show additional examples of the wearable electronic device 100 of FIG. 2A in accordance with further embodiments.

Figure 3:
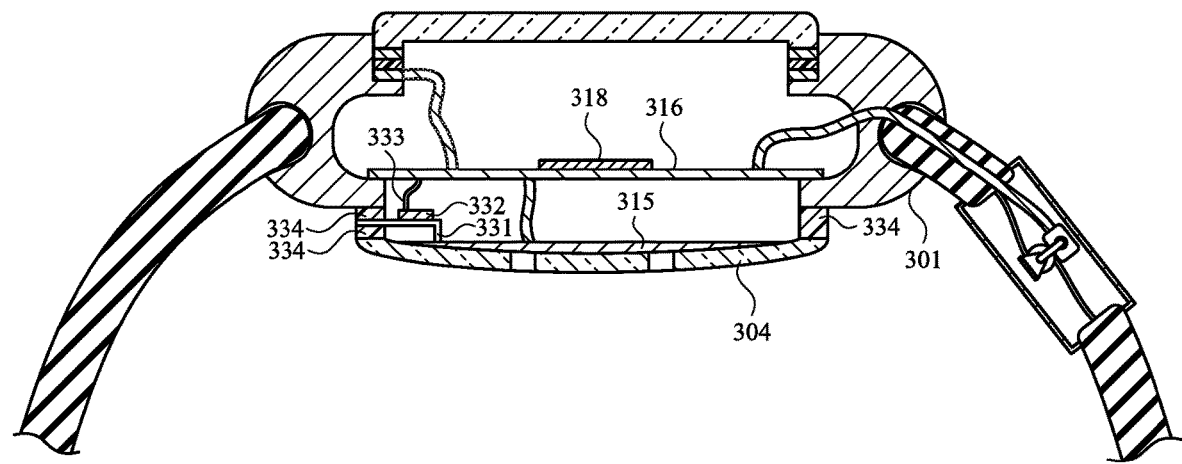
FIGS. 3-7 show additional examples of the wearable electronic device of FIG. 2A in accordance with further embodiments.

FIG. 3 illustrates an example implementation including a deflection element 331 coupled to one or more strain gauges 332. The deflection element 331 may be connected to the health sensor 315 and/or the housing component 304 such that force exerted on the housing component 304 may cause the deflection element 331 to deflect. An electrical property of the strain gauge 332 (e.g., resistance) may change based on the deflection. The processing unit 318 may accordingly receive force signals from the strain gauge 332 via a flex circuit 333 (and/or other electrical or communication connection) and the printed circuit board 316, and may correlate the force signals to an amount of force.

The housing component 304 may be coupled to the main body 301 via adhesive 334. The deflection element 331 may be positioned within the adhesive 334 between the housing component 304 and the main body 301. In some examples, the adhesive 334 may be flexible such that the housing component 304 is operable to move with respect to the main body 301 under the exertion of force to deflect the deflection element 331. In other examples, the adhesive 334 may form a rigid seal and the housing component 304 may be flexible in order to deflect the deflection element 331 under the exertion of force.

Figure 4:
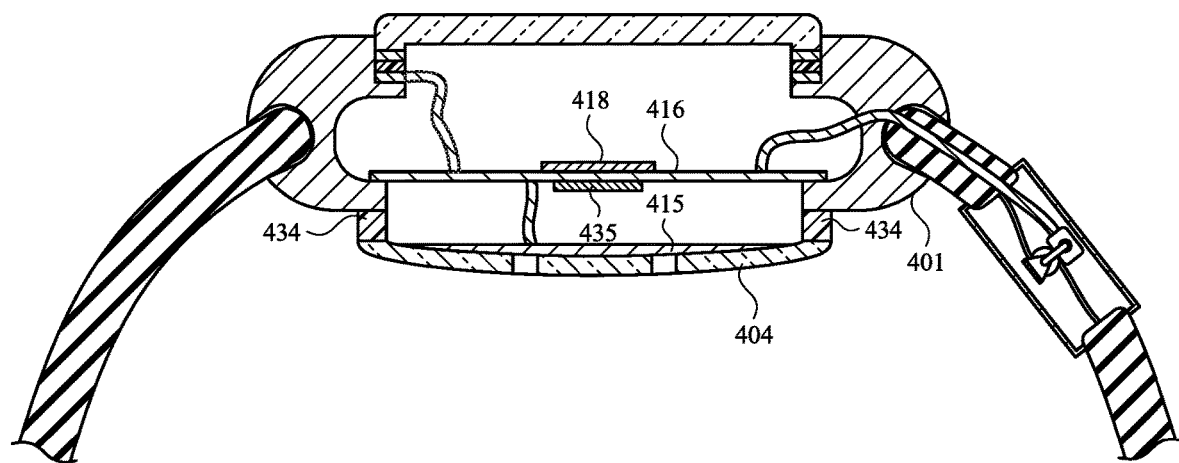

FIG. 4 illustrates an example implementation including a single electrode 435 formed of indium tin oxide or other material positioned on the printed circuit board 416. The single electrode 435 may form a capacitor with the user's body part. Force exerted by the user's body part on the housing component 404 may change the proximity between the user's body part and the electrode 435 thus changing the capacitance of a capacitor formed by the user's body and the electrode 435. The processing unit 418 may receive force signals from such a capacitor indicating capacitive changes and correlate the capacitive changes to an amount of force exerted on the housing component 404.

In some examples, the adhesive 434 and/or the housing component 404 may be flexible. This may allow the user's body to move closer to the electrode 435 under the exertion of force. The more movement that is possible between the user's body and the electrode 435 may allow for a greater variety of capacitance differences of a capacitor formed by the user's body and the electrode 435, allowing for greater sensitivity in sensing force.

Although the electrode 435 is shown as positioned on the printed circuit board 416, it is understood that this is an example. In various implementations, the electrode 435 may be positioned at different locations without departing from the scope of the present disclosure. For example, the electrode 435 may be positioned on the health sensor 415 in some implementations. By way of another example, in various implementations, the electrode 435 may be positioned on the housing component 404 (such as a layer of indium tin oxide, nanostructures, nanomesh, nanowires, a conductive film, and so on deposited on the inner surface of the housing component 404 facing the health sensor 415) or on the main body 401.

Figure 5:
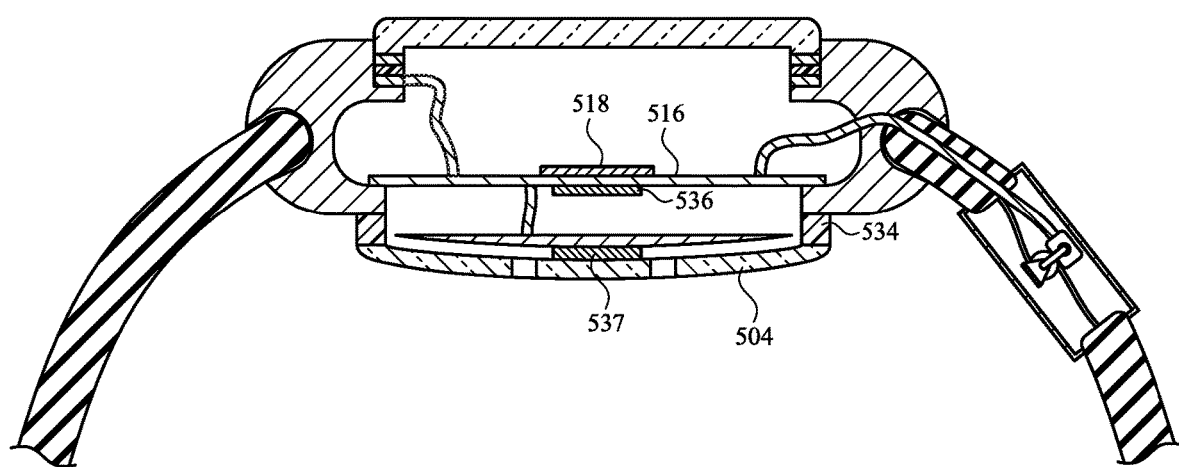

FIG. 5 illustrates an example implementation including a first electrode 536 positioned on the printed circuit board 516 and a second electrode 537 positioned on the housing component 504 that may form a capacitor. An exertion of force on the housing component 504 may bring the first and second electrodes 536 and 537 closer together, changing the capacitance of a capacitor formed by the first and second electrodes 536 and 537. The processing unit 518 may monitor force signals from the first and/or second electrodes 536 and 537 and correlate the capacitance changes to an amount of force exerted on the housing component 504.

In some examples, the adhesive 534 and/or the housing component 504 may be flexible. This may allow the first and second electrodes 536 and 537 to move closer together under the exertion of force on the housing component 504.

Figure 6:
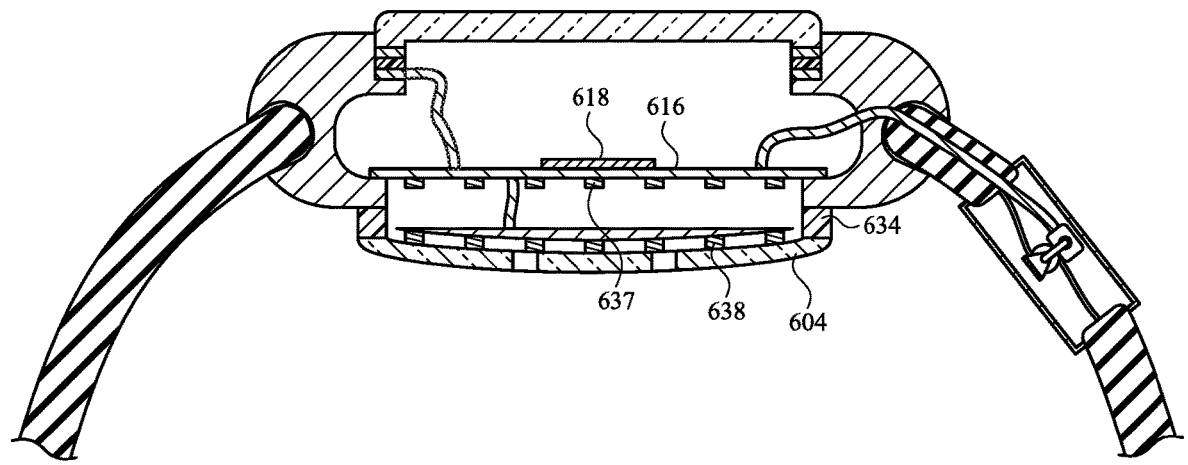

As compared with the example shown in FIG. 5, the example depicted in FIG. 6 includes multiple electrodes 637 (a first set of electrodes 637) positioned on the printed circuit board 616 and multiple electrodes 638 (a second set of electrodes 638) positioned on the housing component 604. Capacitors may be formed by pairs of electrodes of the first set of electrodes 637 and the second set of electrodes 638. A force applied to the housing component 604 may bring one or more electrodes in the first and second sets of electrodes 637 and 638 closer together, and change the respective capacitances of those capacitors. The processing unit 618 may monitor and compare force signals from one or more capacitors in order to correlate respective capacitance changes to amounts of force exerted at various particular locations on the housing component 604.

The adhesive 634 and/or the housing component 604 may be flexible such that the electrodes in the first and second sets of electrodes 637 and 638 may be able to move with respect to each other independently and/or relatively independently based on where force is exerted on the housing component 604. This may enable the processing unit 618 to more granularly determine different amounts of force exerted at different locations on the housing component 604.

Figure 7:
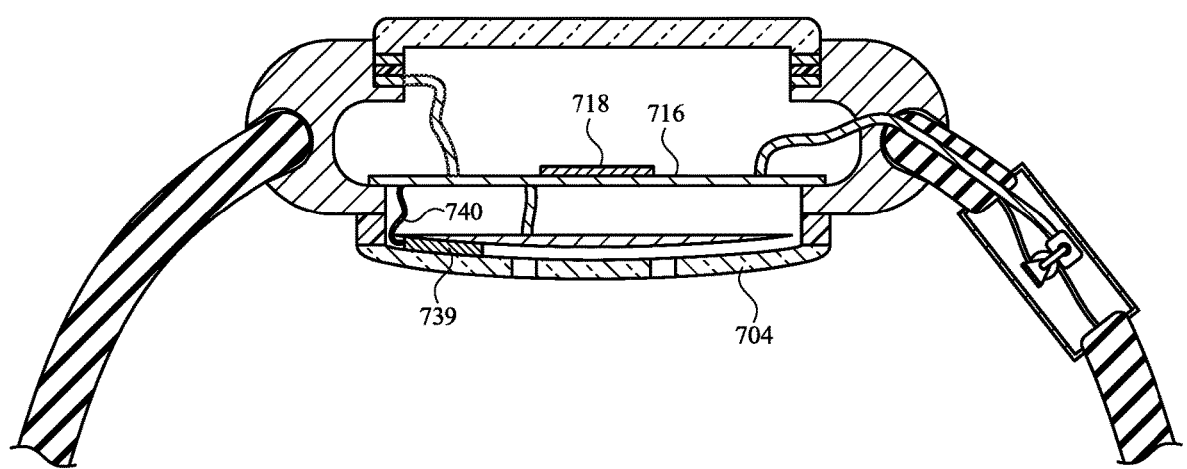

FIG. 7 illustrates an example implementation including a flexible housing component 704 with a strain gauge 739 disposed thereon. An exertion of force on the flexible housing component 704 may cause the flexible housing component 704 to flex, which may cause the strain gauge 739 to deflect. An electrical property of the strain gauge 739 (e.g., resistance) may change based on the deflection. As such, the processing unit 718 may accordingly receive force signals from the strain gauge 739 indicating flexing of the flexible housing component 704 via a flex circuit 740 (and/or other electrical or communication connection) and the printed circuit board 716. The processing unit 718 may correlate the received force signals to force amounts.

Figure 8:
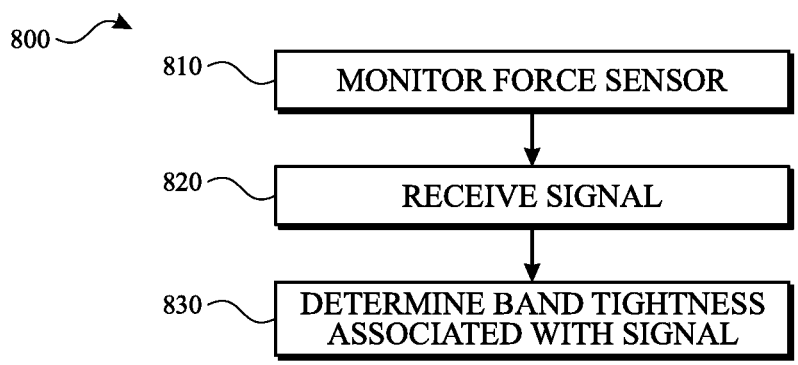
FIG. 8 shows a flow chart illustrating an example method for determining band tightness. This method may be performed by one or more of the wearable electronic devices of FIGS. 1A-7.

FIG. 8 shows a flow chart illustrating an example method 800 for determining band tightness. This method 800 may be performed by one or more of the wearable electronic devices of FIGS. 1A-7.

At 810, a force sensor may be monitored. The force sensor may be positioned between a body of a wearable electronic device and a housing component that contacts a user's body part when the wearable electronic device is worn.

At 820, one or more force signals may be received from the force sensor relating to force exerted on the housing component. The force may be the force exerted on the housing component by the user's body part and may be related to a band of the wearable electronic device causing the user's body part to exert the force based on a tightness of the band.

At 830, the tightness of the band associated with the force signal from the force sensor may be determined. Higher amounts of exerted force indicated by the force signal may correlate to a tighter band. Conversely, lower amounts of exerted force indicated by the force signal may correlate to a looser band.

Although the example method 800 is illustrated and described as including particular operations performed in a particular order, it is understood that this is an example. In various implementations, various orders of the same, similar, and/or different operations may be performed without departing from the scope of the present disclosure.

For example, in various implementations, the example method 800 may include the additional operations related to band adjustment. By way of example, the example method 800 may include the additional operation of determining whether the band tightness is within a tightness range. The tightness range may be a range of force values. In some implementations of such an example, the example method 800 may include the additional operation of causing the band to be adjusted if the band tightness is not within the tightness range. In some cases, the user may be notified prior to adjustment of the band. In such cases, the user may be able to override band adjustment in response to such a notification.

In other implementations, the example method 800 may include the additional operation of notifying the user that the band needs adjustment if the band tightness is not within the tightness range. In such implementations, the user may be prompted to adjust the band.

Figure 9:
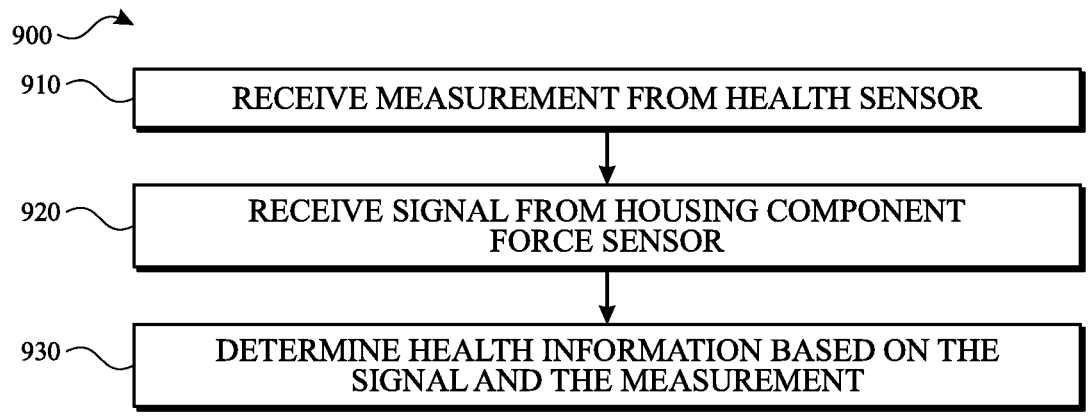
FIG. 9 shows a flow chart illustrating an example method for determining health information using a health sensor and a force sensor. This method may be performed by one or more of the wearable electronic devices of FIGS. 1A-7.

FIG. 9 shows a flow chart illustrating an example method 900 for determining health information using a health sensor and a force sensor. This method 900 may be performed by one or more of the wearable electronic devices of FIGS. 1A-7.

At 910, a measurement may be received from a health sensor. For example, the health sensor may be a PPG sensor.

At 920, a force signal may be received from a housing component force sensor. The housing component force sensor may be positioned between a body of a wearable electronic device and a housing component that contacts a user's body part. The force signal may indicate force exerted on the housing component by the user's body part.

At 930, health information for the user may be determined based on the force signal and the measurement. For example, the force may be used to determine the tightness of a band of the wearable device, which may be used in combination with measurements of a PPG sensor to determine a blood perfusion for the user.

Although the example method 900 is illustrated and described as including particular operations performed in a particular order, it is understood that this is an example. In various implementations, various orders of the same, similar, and/or different operations may be performed without departing from the scope of the present disclosure.

For example, 930 describes the health information as being determined based on the force signal and the measurement. However, in some implementations, the health information may be determined based on the force signal or the measurement without being based on both. Further, the health information may also be based on data from one or more other sensors.

By way of another example, the force may be used to determine whether or not the health information is accurate. In some implementations, the health information may be accurate if the tightness of a band is within a tightness range. In such an example, the force may be used to determine the tightness of the band is within the tightness range. If the tightness of the band is not within the tightness range, the health information may be discarded as inaccurate and/or may be modified based on the force.

Figure 10:
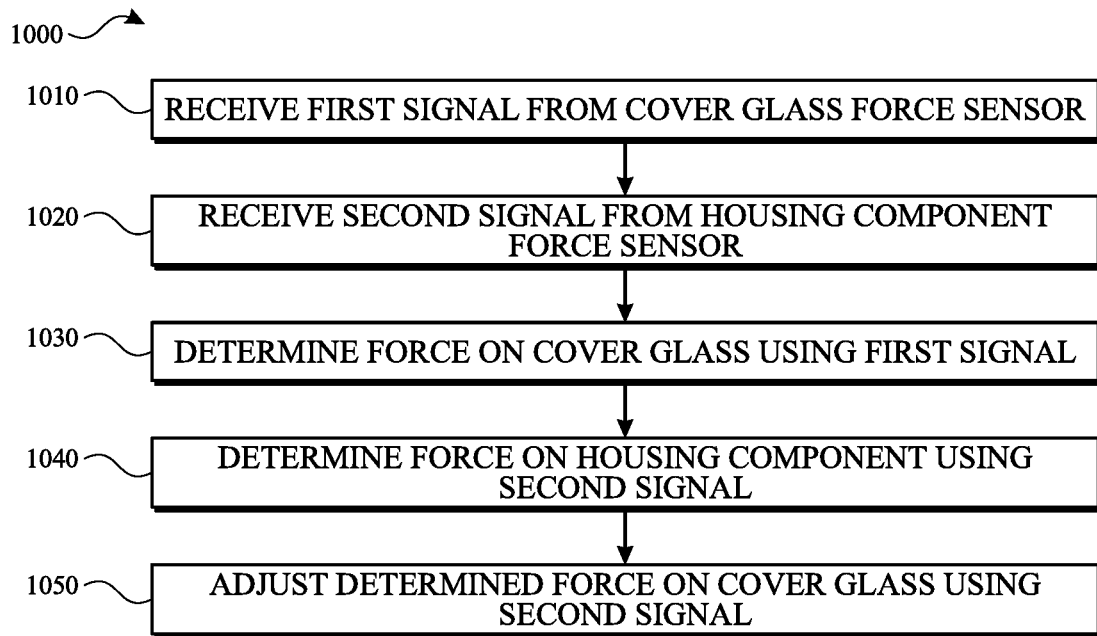
FIG. 10 shows a flow chart illustrating an example method for adjusting detected force determinations. This method may be performed by one or more of the wearable electronic devices of FIGS. 1A-7.

FIG. 10 shows a flow chart illustrating an example method 1000 for adjusting detected force determinations. This method 1000 may be performed by one or more of the wearable electronic devices of FIGS. 1A-7.

At 1010, a first force signal may be received from a cover glass force sensor. The first force signal may indicate a force exerted on the cover glass (or other input device) by a user. The cover glass may be a component of a display, a touch display, and/or other assembly.

At 1020, a second force signal may be received from a housing component force sensor. The housing component force sensor may be positioned between a body of a wearable electronic device and a housing component that contacts a user's body part. The housing component may be positioned on an opposite side of the wearable electronic device from the cover glass. The force signal may indicate force exerted on the housing component by the user's body part.

At 1030, a force exerted on the cover glass may be determined using the first force signal. For example, a lookup table of first force signal values and force values may be consulted based on the first force signal. A force value corresponding to the value of the first force signal may be selected to determine the force exerted on the cover glass.

At 1040, a force exerted on the housing component may be determined using the second force signal. For example, a lookup table of second force signal values and force values may be consulted based on the second force signal. A force value corresponding to the value of the second force signal may be selected to determine the force exerted on the housing component.

At 1050, the determined force on the cover glass may be adjusted using the second force signal. For example, the second force signal may be subtracted from the determined force on the cover glass. This may allow a determined force on the cover glass to be obtained that is free of influence from forces exerted on the housing component.

Although the example method 1000 is illustrated and described as including particular operations performed in a particular order, it is understood that this is an example. In various implementations, various orders of the same, similar, and/or different operations may be performed without departing from the scope of the present disclosure.

For example, 1050 describes the determined force on the cover glass being adjusted using the second force signal. However, in various implementations, the determined force on the housing component may be adjusted using the first force signal instead of and/or in addition to adjusting the determined force on the cover glass using the second force signal.

Figure 11:
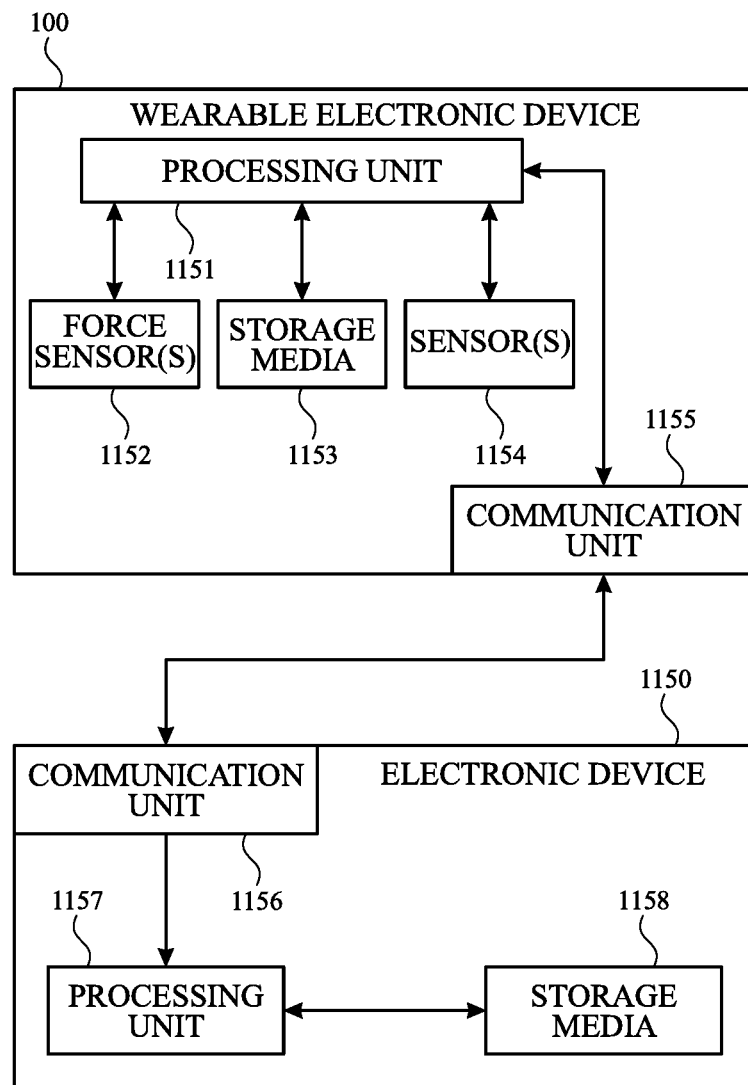
FIG. 11 shows a block diagram illustrating example components that may be utilized in the wearable electronic device and example functional relationships of those components.

FIG. 11 shows a block diagram illustrating example components that may be utilized in the wearable electronic device 100 of FIG. 1A and example functional relationships of those components. The wearable electronic device 100 may include one or more processing units 1151, force sensors 1152 (such as those discussed above), storage media 1153 (such as a magnetic storage medium, an optical storage medium, a magneto-optical storage medium, a read only memory, a random access memory, an erasable programmable memory, and so on), one or more other sensors 1154 (such as one or more health sensors, accelerometers, gyroscopes, light sensors, cameras, proximity sensors, touch sensors, and so on), communication component 1155, and/or other components. The processing unit 1151 may execute instructions stored in the storage media 1153 in order to perform various operations discussed above.

For example, the processing unit 1151 may receive health data from a health sensor 1154 and may store such health data in the storage media 1153. By way of another example, the processing unit 1151 may receive force signals from the force sensor(s) 1152 and may utilize lookup tables stored in the storage media 1153 to correlate force signals to force amounts in order to determine amounts of applied forces, to compare force amounts to threshold force values, to correlate force amounts and/or threshold force values to tightnesses of a band, and so on. The processing unit 1151 may store data regarding such force signals, determined force amounts, determined tightnesses, and so on in the storage media 1153. In examples where the processing unit 1151 determines the tightness of a band, the processing unit 1151 may compare the determined tightness of the band to tightness ranges stored in the storage media 1153 to determine whether or not the determined tightness is within such a range.

The wearable electronic device 100 may communicate with one or more other electronic devices, such as the electronic device 1150, via the communication component 1155 over one or more wired and/or wireless communication connections. Similar to the wearable electronic device 100, the electronic device 1150 may include one or more communication components 1156, processing units 1157, storage media 1158, and/or other components. In various examples, the wearable electronic device 100 may transmit data and/or notifications regarding data to the electronic device 1150 via the communication components 1155 and 1156, such as the above discussed health data, force signals, determined force amounts, determined band tightnesses, and so on. The processing unit 1157 may store such data or notifications in the storage media 1158.

Alternatively and/or additionally, in some examples, the wearable electronic device 100 and the electronic device 1150 may be configured in a cooperative computing arrangement. As such, the electronic device 1150 may utilize the processing unit 1157 to process the data in one or more of the various ways the processing unit 1151 is described processing such data above. For example, the processing unit 1157 may process received health data to determine health information for a user of the wearable electronic device 100. By way of another example, the storage media 1158 may store one or more lookup tables described above. As such, the processing unit 1157 may receive force signals and utilize the lookup tables to correlate force signals to force amounts in order to determine amounts of applied forces, to compare force amounts to threshold force values, to correlate force amounts and/or threshold force values to tightnesses of a band, and so on. The processing unit 1157 may store the results of such determinations in the storage media 1158, transmit such results to the wearable electronic device 100, and/or perform various other operations Although the present disclosure is described as positioning force sensors between a housing component and a main body, it is understood that these are examples. In various implementations, force sensors may be positioned anywhere on a wearable electronic device that contacts a user's body part when the wearable electronic device is worn without departing from the scope of the present disclosure. For example, a force sensor may be positioned on an inner surface of a band that contacts a user's body part when the electronic device is worn. By way of another example, a force sensor may be positioned on an outer surface of the housing component that contacts a user's body part when the wearable electronic device is worn. By way of still another example, a force sensor may be positioned on a portion of the main body that contacts a user's body part when the wearable electronic device is worn.

Further, although the present disclosure is described in the context of a wearable electronic device 100, it is understood that this is an example. The force sensors and/or other techniques discussed herein may be used with other devices (electronic, non-electronic, non-wearable, portable, and so on), such as the back of a smart phone, supports attached to the bottom of a laptop computer, and/or any other device without departing from the scope of the present disclosure.

As described above and illustrated in the accompanying figures, a wearable electronic device may include a body, a housing component (such as a plate, a curved plate, or other surface component), and a band or other attachment mechanism operable to attach the body to the body part of a user. A force sensor may be positioned between the housing component and the body such that it produces force signals based on a force exerted between the user's body part and the housing component. A processing unit may receive the force signals and process them to perform various actions. For example, the processing unit may process the force signals to determine a tightness of the band, such as for automatic band adjustment. By way of another example, the processing unit may use the force signals to determine health information for the user, such as in combination with measurements of the body part obtained via a health sensor included in the body. By way of still another example, the body may include an input mechanism (such as a touch surface including a cover glass) that interprets the force of a user's touch as input and the processing unit may use the force signals and signals from the input mechanism to adjust determinations of force applied to the housing component or input mechanism. Various uses for the force signals from the force sensor are possible and contemplated.

In the present disclosure, the methods disclosed may be implemented as sets of instructions or software readable by a device. Further, it is understood that the specific order or hierarchy of steps in the methods disclosed are examples of sample approaches. In other embodiments, the specific order or hierarchy of steps in the method can be rearranged while remaining within the disclosed subject matter. The accompanying method claims present elements of the various steps in a sample order, and are not necessarily meant to be limited to the specific order or hierarchy presented.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A wearable electronic device, comprising:
   a main watch housing;
   a back plate coupled to the main watch housing;
   a watch band coupled to the main watch housing;
   a force sensor that produces a force signal in response to a force exerted on the back plate, wherein the back plate is coupled to the main watch housing via the force sensor; and
   a processing unit, communicably coupled to the force sensor, that determines a tightness of the watch band using the force signal.

2. The wearable electronic device of claim 1, wherein the force sensor comprises a strain gauge.

3. The wearable electronic device of claim 1, wherein the force sensor comprises a pair of electrodes separated by a deformable material.

4. The wearable electronic device of claim 1, wherein:
   the force sensor includes an electrode; and
   the force signal indicates a capacitance between the electrode and an object.

5. The wearable electronic device of claim 4, wherein the electrode comprises indium tin oxide.

6. The wearable electronic device of claim 1, wherein the force sensor functions as a gasket between the main watch housing and the back plate.

7. The wearable electronic device of claim 1, further comprising a circuit board disposed within the main watch housing, wherein:
   the force signal indicates a capacitance between a first electrode coupled to the back plate and a second electrode coupled to the circuit board.

8. The wearable electronic device of claim 7, wherein the first electrode comprises a first set of electrodes and the second electrode comprises a second set of electrodes.

9. The wearable electronic device of claim 7, wherein the back plate is flexible.

10. A wearable electronic device, comprising:
    a watch body comprising a main housing and a plate that is configured to be positioned adjacent a body part of a user when the watch body is worn;

a health sensor, disposed within the main housing, that is configured to obtain a measurement of the body part of the user;

a force sensor that produces a force signal in response to a force exerted between the body part of the user and the plate, wherein the plate is coupled to the main housing via the force sensor; and a processing unit, communicably coupled to the force sensor, that determines health information for the user using the force signal received from the force sensor and the measurement obtained by the health sensor.

11. The wearable electronic device of claim 10, wherein the processing unit determines whether the measurement obtained by the health sensor is accurate using the force signal.

12. The wearable electronic device of claim 11, further comprising a watch band coupled to the main housing; wherein the processing unit:

determines a tightness of the watch band using the force signal;

determines whether the tightness of the watch band is within a range of force values; and determines whether the measurement is accurate using the determination of whether the tightness of the watch band is within the range of force values.

13. The wearable electronic device of claim 10, wherein the health information includes at least one of a swelling indication, a blood pressure, a body fat indication, an allergic reaction indication, a hydration indication, or an edema indication.

14. The wearable electronic device of claim 10, further comprising:

a watch band coupled to the main housing; and a band tightness adjustment mechanism; wherein:

the processing unit causes a tightness of the watch band determined using the force signal to be altered using the band tightness adjustment mechanism.

15. The wearable electronic device of claim 14, wherein the processing unit provides a notification to the user by causing the tightness of the watch band to be altered.

16. A wearable electronic device, comprising:

a main watch housing;

a band coupled to the main watch housing;

a plate coupled to the main watch housing;

a photoplethysmogram (PPG) sensor, disposed within the main watch housing, that obtains a measurement;

a force sensor that produces a force signal indicating a tightness of the band, wherein the plate is coupled to the main watch housing via the force sensor; and a processing unit, communicably coupled to the force sensor, that determines when the measurement is accurate using the tightness of the band.

17. The wearable electronic device of claim 16, wherein the processing unit determines the measurement is accurate when the tightness of the band is within a range.

18. The wearable electronic device of claim 16, wherein the processing unit uses the PPG sensor to obtain an additional measurement upon determining that the measurement is inaccurate.

19. The wearable electronic device of claim 16, wherein the processing unit disregards the measurement upon determining that the measurement is inaccurate.

20. The wearable electronic device of claim 16, wherein the processing unit determines the measurement is accurate when the tightness of the band is outside a range.

* * * * *